(12) United States Patent
Park et al.

(10) Patent No.: US 7,351,560 B2
(45) Date of Patent: Apr. 1, 2008

(54) **GLYCEROL-3-PHOSPHATE PHOSPHATASE AND GLYCEROL-3-PHOSPHATE DEHYDROGENASE FROM *CANDIDA ALBICANS*, GENES ENCODING THE SAME, VECTOR AND HOST CELL CONTAINING THE GENES, AND METHOD FOR PRODUCING GLYCEROL USING THE HOST CELL**

(75) Inventors: Young Hoon Park, Seongnam (KR); Kwang Myung Cho, Icheon (KR); Hye Won Um, Suwon (KR)

(73) Assignee: CJ Corp., Seoul (KR)

( * ) Notice: Subject to any disclaimer, the term of this patent is extended or adjusted under 35 U.S.C. 154(b) by 176 days.

(21) Appl. No.: 10/558,764

(22) PCT Filed: May 28, 2004

(86) PCT No.: PCT/KR2004/001263

§ 371 (c)(1),
(2), (4) Date: Nov. 29, 2005

(87) PCT Pub. No.: WO2004/106507

PCT Pub. Date: Dec. 9, 2004

(65) Prior Publication Data

US 2007/0020742 A1    Jan. 25, 2007

(30) Foreign Application Priority Data

Jun. 3, 2003   (KR) ................. 10-2003-0035691

(51) Int. Cl.
| | |
|---|---|
| *C12P 7/20* | (2006.01) |
| *C12N 1/21* | (2006.01) |
| *C12N 15/63* | (2006.01) |
| *C12N 9/04* | (2006.01) |
| *C12N 9/16* | (2006.01) |
| *C07H 21/04* | (2006.01) |

(52) U.S. Cl. .............. 435/159; 435/190; 435/196; 435/252.33; 435/320.1; 536/23.2

(58) Field of Classification Search ............. None
See application file for complete search history.

(56) References Cited

U.S. PATENT DOCUMENTS 6,358,716 B1    3/2002   Bulthuis et al.
6,747,137 B1 *  6/2004   Weinstock et al. ......... 536/23.1

OTHER PUBLICATIONS

Jones et al. (May 11, 2004) PNAS, vol. 101, No. 19, pp. 7329-7334.*
Wang, H. et al., "Cloning, Sequence, and Disruption of the *Saccharomyces diastaticus* DAR1 Gene Encoding a Glycerol-3-Phosphate Dehydrogenase", Journal of Bacteriology, 176, No. 22, Nov. 1994, pp. 7091-7095.
Redkar, R., et al., Biosynthetic Pathways of Glycerol Accumulation under Salt Stress in *Aspergillus nidulans*, Experimental Mycology 19, 1995, pp. 241-246.

* cited by examiner

*Primary Examiner*—Elizabeth Slobodyansky
(74) *Attorney, Agent, or Firm*—Rothwell, Figg, Ernst & Manbeck

(57) ABSTRACT

Provided are a polypeptide having glycerol-3-phosphate dehydrogenase activity and a 80% or more homology to an amino acid sequence as set forth in SEQ ID NO: 1 and a polypeptide having glycerol-3-phosphate phosphatase activity and a 80% or more homology to an amino acid sequence as set forth in SEQ ID NO: 2. Provided is also a method for producing glycerol, which includes: culturing a host cell transformed with a vector containing a polynucleotide including a first polynucleotide encoding an amino acid sequence as set forth in SEQ ID NO: 1 and a second polynucleotide encoding an amino acid sequence as set forth in SEQ ID NO: 2 which are operably linked to a suitable regulatory sequence; and recovering glycerol from the culture.

6 Claims, 2 Drawing Sheets

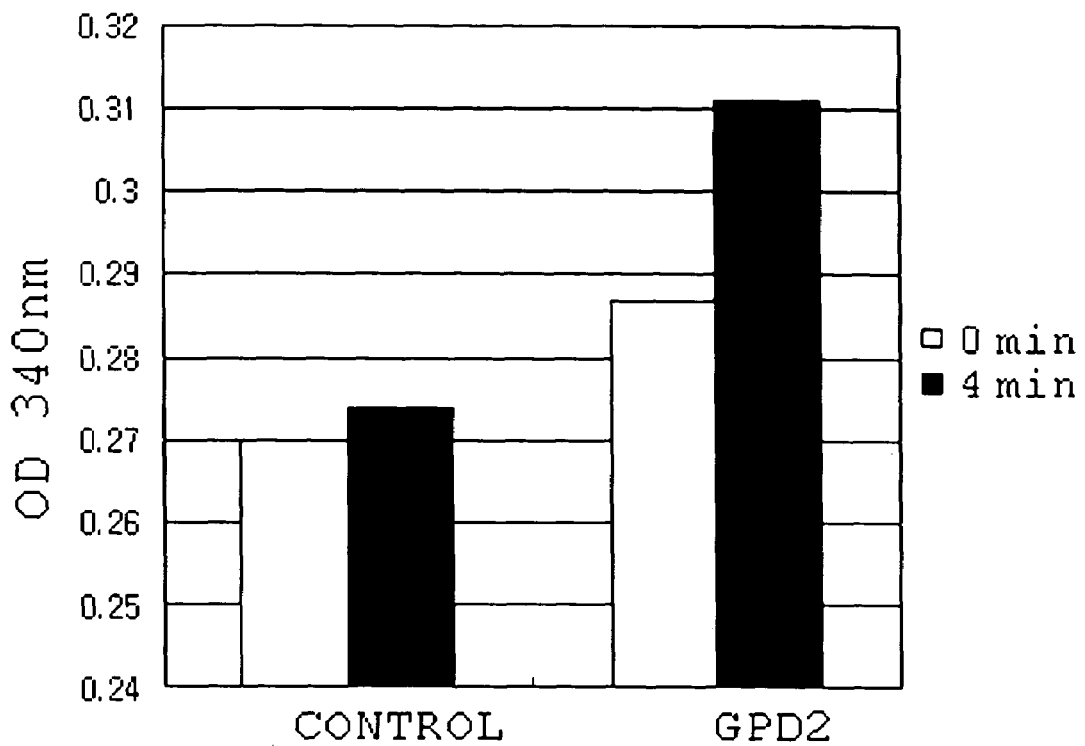
[Fig. 1]
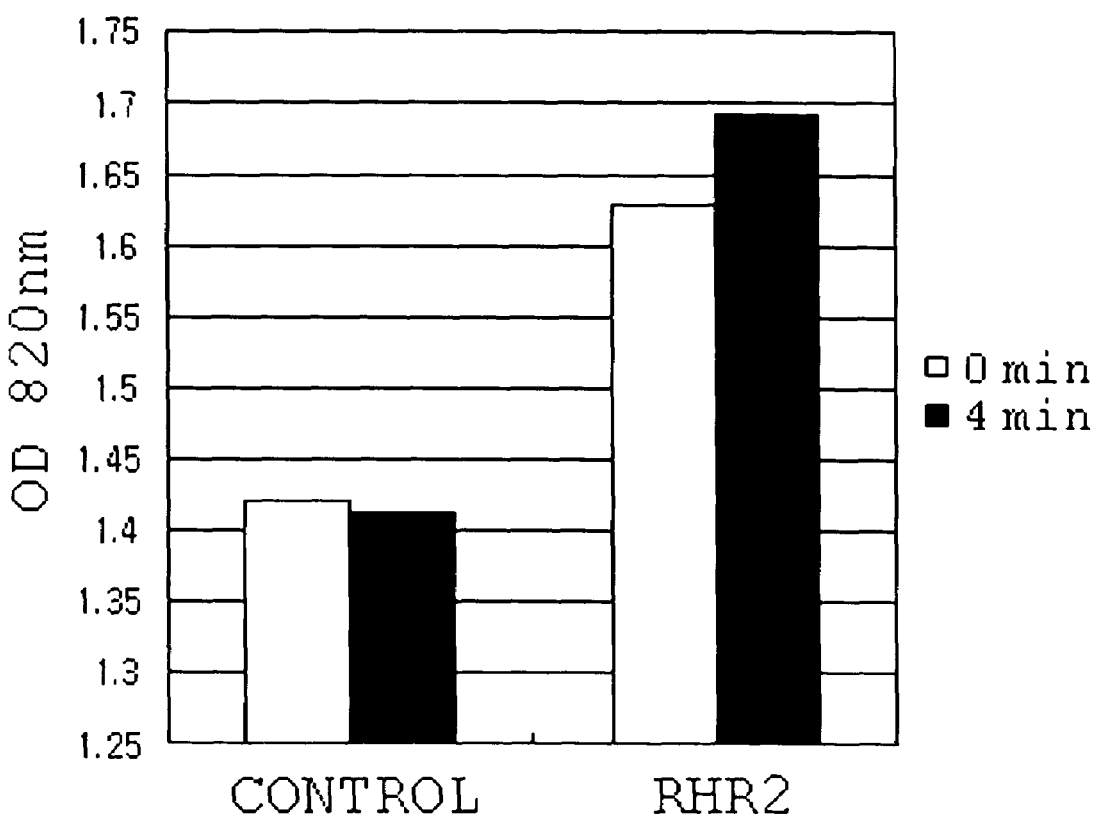
[Fig. 2]

SEQUENCE LISTING

<160> NUMBER OF SEQ ID NOS: 14

<210> SEQ ID NO 1
<211> LENGTH: 371
<212> TYPE: PRT
<213> ORGANISM: Candida albicans

<400> SEQUENCE: 1

```
Met Thr Thr Ser Pro Tyr Pro Ile Glu Thr Pro Phe Lys Val Cys Ile
  1               5                  10                  15

Val Gly Ser Gly Asn Trp Gly Thr Ala Val Ala Lys Leu Val Ala Glu
             20                  25                  30

Asn Cys Ala Glu Lys Pro Asn Ile Phe Gln Arg Asp Val Lys Met Trp
         35                  40                  45

Val Phe Glu Glu Glu Ile Glu Gly Arg Lys Leu Thr Glu Ile Ile Asn
     50                  55                  60

Thr Glu His Glu Asn Val Lys Tyr Leu Pro Glu Ile Lys Leu Pro Thr
 65                  70                  75                  80

Asn Leu Val Ala Asn Pro Asp Ile Val Asp Thr Val Gln Asp Ala Asp
                 85                  90                  95

Leu Ile Val Phe Asn Ile Pro His Gln Phe Leu Gly Arg Ile Val Lys
            100                 105                 110

Gln Ile Glu Gly Lys Val Lys Pro Thr Ala Arg Ala Ile Ser Cys Leu
        115                 120                 125

Lys Gly Leu Asp Val Ser Pro Glu Gly Cys Lys Leu Leu Ser Thr Ser
130                 135                 140

Ile Thr Asp Thr Leu Lys Ile Tyr Cys Gly Val Leu Ser Gly Ala Asn
145                 150                 155                 160

Ile Ala Asn Glu Val Ala Lys Gly Asn Trp Ser Glu Thr Ser Ile Ala
                165                 170                 175

Tyr Thr Val Pro Glu Asp Phe Arg Gly Ala Gly Lys Asp Ile Asp Pro
            180                 185                 190

Phe Ile Leu Lys Glu Ala Phe His Arg Pro Tyr Phe His Val Arg Val
        195                 200                 205

Ile Glu Asp Val Val Gly Ala Ser Ile Ala Gly Ala Leu Lys Asn Val
    210                 215                 220

Ile Ala Cys Ser Val Gly Phe Val Glu Gly Ala Gly Trp Gly Asp Asn
225                 230                 235                 240

Ala Lys Ala Ala Ile Met Arg Ile Gly Ile Lys Glu Thr Ile Arg Phe
                245                 250                 255

Ala Ser Tyr Trp Glu Leu Phe Lys Ile Lys Ala Leu Ser Pro Pro Asn
            260                 265                 270

Pro Lys Thr Phe Thr Glu Glu Ser Ala Gly Val Ala Asp Leu Ile Thr
        275                 280                 285

Thr Cys Ser Gly Gly Arg Asn Val Lys Val Ala Arg Tyr Met Ile Lys
    290                 295                 300

Asn Asn Val Asp Ala Phe Glu Ala Glu Lys Ile Val Leu Lys Gly Gln
305                 310                 315                 320

Ser Ser Gln Gly Ile Leu Thr Ala Lys Glu Val His Glu Leu Leu Thr
                325                 330                 335

Asn Phe Asn Leu Gln Asp Glu Phe Pro Leu Leu Glu Ala Thr Tyr Lys
            340                 345                 350

Val Ile Tyr Glu Asn Gly Ser Val Asp Asp Phe Pro Gln Leu Leu Glu
```

355                 360                 365
Gly Asp Gln
    370

<210> SEQ ID NO 2
<211> LENGTH: 254
<212> TYPE: PRT
<213> ORGANISM: Candida albicans

<400> SEQUENCE: 2

Met Thr Lys Thr Gln Gln Pro Ala Val Phe Tyr Val His Ala Ala Leu
 1               5                  10                  15

Phe Asp Cys Asp Gly Thr Leu Val Asn Ser Thr Gly Ala Ile Ser Glu
            20                  25                  30

Phe Trp Arg Asp Phe Gly Lys Thr Arg Pro His Val Asp Pro Glu Glu
        35                  40                  45

Ile Ile Arg Thr Ser His Gly Cys Arg Thr Phe Asp Val Ile Ala Lys
    50                  55                  60

Trp Ser Pro Glu Asp Ala Ile Glu Glu Gln Val Thr Ala Trp Glu Gly
65                  70                  75                  80

Ala Ile Pro Asp Thr Phe Gly His His Ala Lys Pro Ile Pro Gly Ser
                85                  90                  95

Val Glu Leu Val Lys Ser Phe Asp Lys Leu Ser Lys Glu Ala Thr Glu
            100                 105                 110

Asn Gly Lys Gln Arg Trp Ala Val Val Thr Ser Gly Thr Leu Pro Leu
        115                 120                 125

Ala Thr Lys Trp Leu Lys Leu Leu Ser Ile Glu Arg Pro Asp Cys Phe
    130                 135                 140

Ile Thr Ala Glu Lys Val Thr Lys Gly Lys Pro His Pro Gln Gly Tyr
145                 150                 155                 160

Gln Ala Ala Arg Asp Thr Leu Gly Tyr His Asp Ala His Tyr Lys Val
                165                 170                 175

Val Val Phe Glu Asp Ala Pro Ala Gly Ile Thr Ala Gly Lys Gly Ala
            180                 185                 190

Gly Ala Met Val Val Gly Ile Cys Ser Thr Tyr Asp Pro Glu Lys Val
        195                 200                 205

Arg Lys Ser Gly Ala Asn Ile Val Val Lys Asp Leu Ser Ser Phe Arg
    210                 215                 220

Ile Asp Ser Tyr Asn Lys Glu Thr Asp Glu Phe Lys Val Val Val Asp
225                 230                 235                 240

Asp Tyr Phe Tyr Ala Asp Glu Gln Phe Leu Gln Glu Ser Ala
                245                 250

<210> SEQ ID NO 3
<211> LENGTH: 1116
<212> TYPE: DNA
<213> ORGANISM: Candida albicans

<400> SEQUENCE: 3
atgactactt cccatatcc aattgaaact ccatttaaag tttgtattgt cggttccggt      60
aactggggta ctgcagttgc aaaattagtt gctgaaaact gtgctgaaaa accaaatatt    120
ttccaaagag acgttaaaat gtgggttttc gaagaagaaa ttgaaggtag aaaattgaca    180
gaaataatta acaccgaaca tgaaaatgtt aaatacttgc agaaattaa attgccaact     240 aacttggttg ccaacccaga cattgttgac actgttcaag atgccgactt gattgttttc    300

```
aatattccac atcaattctt gggtagaatt gtcaaacaaa tcgaaggtaa agtgaaacca      360
actgctagag ccatttcatg tttgaaaggt ttggatgtga gtccagaagg ttgcaaattg      420
ttgtcaacct ctatcactga tactttgaag atttactgtg gtgtcttatc tggtgctaat      480
attgccaacg aagttgccaa aggtaactgg tcagaaactt ccattgccta cactgttcca      540
gaagatttca gaggtgccgg taaagatatt gatccattta ttttgaaaga agctttccac      600
agaccatact tccatgtcag agttattgaa gatgttgttg gtgcctctat tgctggtgcc      660
ttaaagaatg tcattgcctg ttctgttggt ttcgttgaag gtgctggctg gggtgacaat      720
gctaaagctg ctattatgag aatcggtatc aagaaaacca tccgttttgc ttcttactgg      780
gaattgttca agatcaaggc tttgtctcca ccaaacccaa aaactttcac cgaagaaagt      840
gctggtgttg ctgatttgat cactacttgc tcaggtggta gaaatgttaa agtcgccaga      900
tacatgatta aaaacaatgt cgatgcattt gaagctgaaa aaattgtttt gaaaggacaa      960
agttctcaag gtatcttgac tgccaaagaa gttcacgaat tgttaacaaa tttcaaccttt    1020 caagacgaat tcccattact cgaagccacc tataaagtta tctacgagaa tggtagtgtt     1080
gacgatttcc cacaattatt agaaggtgat caataa                               1116

<210> SEQ ID NO 4
<211> LENGTH: 765
<212> TYPE: DNA
<213> ORGANISM: Candida albicans

<400> SEQUENCE: 4
atgacaaaga ctcaacaacc agctgttttt tacgttcacg ccgctttatt tgactgtgat       60
ggtactttgg ttaactccac tggtgctatt tctgaattct ggagagattt cggaaaaact      120
agacctcatg ttgatccaga agaaattatc agaacttccc atggttgccg tacatttgat      180
gtcattgcca aatggtcacc agaagatgca attgaagaac aagtcactgc atgggaaggt      240
gctattcctg acacttttgg ccaccacgcc aagccaattc caggttccgt tgaattggta      300
aaatcattcg ataaactttc taagaagct actgaaaatg gtaaacaaag atgggctgtt      360
gtcacttctg gtactttgcc attagccacc aaatggttga aattattgtc tattgaaagg      420
ccagactgtt ttataaccgc tgaaaaagtg actaaaggta aaccacatcc acaaggttac      480
caagctgcta gagatacttt gggataccat gacgcccact acaaagttgt tgtgtttgaa      540
gacgctccag ctggtataac cgcaggtaaa ggtgctggcg ccatggttgt cggtatttgc      600
tcaacttacg atcctgaaaa agttagaaaa tcaggtgcta acattgttgt caagattta      660 tccagcttta gaatcgactc atacaacaag gaaactgacg aattcaaggt tgttgttgat      720
gattatttct acgctgatga gcaattttta caagaatctg cttaa                     765

<210> SEQ ID NO 5
<211> LENGTH: 24
<212> TYPE: DNA
<213> ORGANISM: Artificial Sequence
<220> FEATURE:
<223> OTHER INFORMATION: forward primer for GPD2 amplification from
      Candida albicans

<400> SEQUENCE: 5
cccatcttgt tccacaattt tact                                             24

<210> SEQ ID NO 6
<211> LENGTH: 24
<212> TYPE: DNA
```

```
<213> ORGANISM: Artificial Sequence
<220> FEATURE:
<223> OTHER INFORMATION: reverse primer for GPD2 amplification from
      Candida albicans

<400> SEQUENCE: 6
tgtacaaaac agtgatatca ctgc                                          24

<210> SEQ ID NO 7
<211> LENGTH: 24
<212> TYPE: DNA
<213> ORGANISM: Artificial Sequence
<220> FEATURE:
<223> OTHER INFORMATION: forward primer for RHR2 amplification from
      Candida albicans

<400> SEQUENCE: 7
ccaatgattt ccacattcgt aaaa                                          24

<210> SEQ ID NO 8
<211> LENGTH: 24
<212> TYPE: DNA
<213> ORGANISM: Artificial Sequence
<220> FEATURE:
<223> OTHER INFORMATION: revers primer for RHR2 amplification from
      Candida albicans

<400> SEQUENCE: 8
tagcggacca ttttacacac aatt                                          24

<210> SEQ ID NO 9
<211> LENGTH: 24
<212> TYPE: DNA
<213> ORGANISM: Artificial Sequence
<220> FEATURE:
<223> OTHER INFORMATION: forward primer for GPD2 amplification from
      pCR2.1-GPD2 vector

<400> SEQUENCE: 9
gctagcaatg actacttccc cata                                          24

<210> SEQ ID NO 10
<211> LENGTH: 24
<212> TYPE: DNA
<213> ORGANISM: Artificial Sequence
<220> FEATURE:
<223> OTHER INFORMATION: reverse primer for GPD2 amplification from
      pCR2.1-GPD2 vector

<400> SEQUENCE: 10
ctcgagaccc atttattgat cacc                                          24

<210> SEQ ID NO 11
<211> LENGTH: 24
<212> TYPE: DNA
<213> ORGANISM: Artificial Sequence
<220> FEATURE:
<223> OTHER INFORMATION: forward primer for RHR2 amplification from
      pCR2.1-RHR2

<400> SEQUENCE: 11
gctagcaatg acaaagactc aaca                                          24

<210> SEQ ID NO 12
<211> LENGTH: 24
<212> TYPE: DNA
<213> ORGANISM: Artificial Sequence
```

```
<220> FEATURE:
<223> OTHER INFORMATION: reverse primer for RHR2 amplification from
      pCR2.1-RHR2

<400> SEQUENCE: 12
ctcgagttaa gcagattctt gtaa                                          24

<210> SEQ ID NO 13
<211> LENGTH: 24
<212> TYPE: DNA
<213> ORGANISM: Artificial Sequence
<220> FEATURE:
<223> OTHER INFORMATION: forward primer containing NdeI site

<400> SEQUENCE: 13
catatgttgc gccgacatca taac                                          24

<210> SEQ ID NO 14
<211> LENGTH: 24
<212> TYPE: DNA
<213> ORGANISM: Artificial Sequence
<220> FEATURE:
<223> OTHER INFORMATION: reverse primer containing NdeI site

<400> SEQUENCE: 14
catatgtgtc tcatgagcgg atac                                          24
```

GLYCEROL-3-PHOSPHATE PHOSPHATASE AND GLYCEROL-3-PHOSPHATE DEHYDROGENASE FROM *CANDIDA ALBICANS*, GENES ENCODING THE SAME, VECTOR AND HOST CELL CONTAINING THE GENES, AND METHOD FOR PRODUCING GLYCEROL USING THE HOST CELL

TECHNICAL FIELD

The present invention relates to a polypeptide having glycerol-3-phosphate dehydrogenase activity, a polypeptide having glycerol-3-phosphate phosphatase activity, polynucleotides encoding the polypeptides, a vector and a host cell containing the polynucleotides, and a method for producing glycerol using the host cell.

BACKGROUND ART

Glycerol is used as an intermediate for various industrial products such as cosmetics, liquid soaps, foods, medicines, and lubricants, and as a material for the fermentation industry. For example, 1,3-propanediol is produced by fermentation of glycerol.

Glycerol can be produced by fermentation, chemical synthesis, or lipolysis. With respect to glycerol production by microorganism fermentation, yeasts such as *S. cerevisiae, C. magnoliae, P. farinose,* and *C. glycerinogenes,* bacteria such as *B. subtilis,* and algae such as *D. tertiolecta* are known as a glycerol-producing microorganism.

It is known that a recombinant microorganism developed by manipulating a known glycerol biosynthetic pathway can be used as a glycerol-producing microorganism.

Generally, a carbon substrate such as glucose is converted to glucose-6-phosphate by hexokinase in the presence of ATP. Glucose-6-phosphate is converted to fructose-6-phosphate by glucose-phosphate isomerase, which is then converted to fructose-1,6-diphosphate by 6-phosphofructokinase. Fructose-1,6-diphosphate is converted to dihydroxyacetone phosphate (DHAP) by aldolase. Finally, DHAP is converted to glycerol-3-phosphate (G3P) by NADH-dependent glycerol-3-phosphate dehydrogenase (G3PDH), which is then dephosphorylated to glycerol by glycerol-3-phosphate phosphatase (Agarwal (1990), Adv. Biochem. Engrg. 41:114).

In addition, an alternative pathway for glycerol production from DHAP has been suggested (Wang et al., 1994 J. Bact. 176: 7091-7095). According to this alternative pathway for glycerol production, DHAP is dephosphorylated to dihydroxyacetone by specific or nonspecific phosphatase, which is then reduced to glycerol by dihydroxyacetone reductase. Dihydroxyacetone reductase is found in prokaryotes and *Schizosaccharomyces pombe*. Another alternative pathway for glycerol production from DHAP has been suggested (Redkar, Experimental Mycology, 19: 241, 1995). According to this alternative pathway for glycerol production, DHAP is isomerized to glyceraldehyde-3-phosphate by triose 3-phosphate isomerase which is a common glycolysis enzyme. Glyceraldehyde-3-phosphate is dephosphorylated to glyceraldehyde, which is then reduced by alcohol dehydrogenase or NADPH-dependent glycerol dehydrogenase.

Among genes that participate in a known glycerol biosynthetic pathway, DAR1 and GPD1 from *S. cerevisiae* is known as a gene encoding G3PDH for conversion of DHAP to G3P. GPP2 from *S. cerevisiae* is known as a gene encoding glycerol-3-phosphate phosphatase for conversion of G3P to glycerol.

In addition, there is known a method for producing glycerol using a recombinant host cell obtained by introducing a foreign gene involved in glycerol synthesis into a host cell dependent on a natural glycerol synthetic pathway. For example, U.S. Pat. No. 6,358,716 discloses a method for producing glycerol from a recombinant microorganism, which includes: (i) transforming a suitable host cell with an expression cassette including (a) a gene encoding NADH-dependent glycerol-3-phosphate dehydrogenase or NADPH-dependent glycerol-3-phosphate dehydrogenase; and (b) a gene encoding glycerol-3-phosphate phosphatase (EC 3.1.3.21); (ii) culturing the transformed host cell of (i) in the presence of at least one carbon source selected from the group consisting of monosaccharides, oligosaccharides, polysaccharides, and single-carbon substrates, to thereby produce glycerol; and (iii) recovering the glycerol produced in (ii).

DESCRIPTION OF DRAWINGS

FIG. 1 illustrates the result of activity measurement of glycerol-3-phosphate dehydrogenase.

FIG. 2 illustrates the result of activity measurement of glycerol-3-phosphate phosphatase.

BEST MODE

Figure 3:
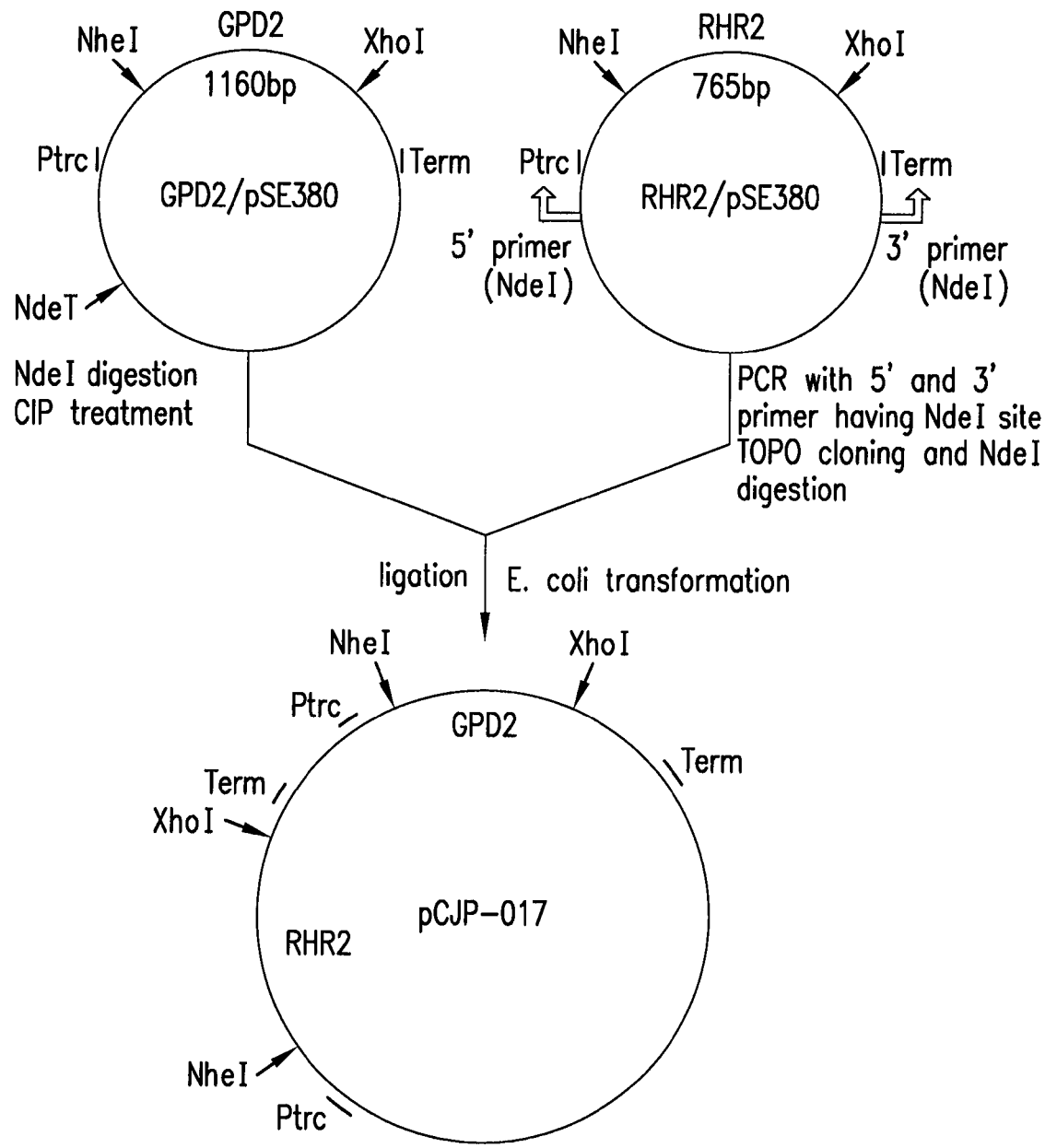
FIG. 3 illustrates a construction scheme for a vector containing a polynucleotide in which a polynucleotide encoding glycerol-3-phosphate dehydrogenase and a polynucleotide encoding glycerol-3-phosphate phosphatase are operably linked to a suitable regulatory sequence.

Hereinafter, the present invention will be described more specifically by Examples. However, the following Examples are provided only for illustrations and thus the present invention is not limited to or by them.

EXAMPLE 1

Selection of Novel Genes

In this Example, a homology search of GPD1 (NCBI X76859, SGD GPD1/YDL022W) which is a gene of glycerol-3-phosphate dehydrogenase (G3PDH) of *Saccharomyces cerevisiae* that catalyzes the conversion of dihydroxyacetone phosphate (DHAP) to glycerol 3-phosphate (G3P) and GPP2 (SGD HOR2/YER062C) which is a gene of glycerol 3-phosphate phosphatase of *Saccharomyces cerevisiae* that catalyzes the conversion of G3P to glycerol was performed using BLAST program provided by the National Center of Biotechnology Information (NCBI) in U.S.A. (www.ncbi.nlm.nih.gov) to select genes that have significant homology but unknown functions. The selected genes were GPD2 (SEQ ID NO: 3, CA0824) and RHR2 (SEQ ID NO: 4, CA5788) from *Candida albicans*.

EXAMPLE 2

Subcloning of GPD2 and RHR2 Genes of *Candida albicans*

*Candida albicans* (KCTC7270) was distributed from the Korean Collection for Type Cultures (KCTC) of Korea Research Institute of Bioscience and Biotechnology and its genomic DNA was extracted from the strain. GPD2 was amplified by PCR using the genomic DNA as a template and a pair of oligonucleotides having nucleotide sequences of SEQ ID NOS: 5 and 6 as primers. Also, RHR2 was amplified by PCR using the genomic DNA as a template and a pair of oligonucleotides having nucleotide sequences of SEQ ID NOS: 7 and 8 as primers.

Respective amplified products of GPD2 and RHR2 were cloned into pCR2.1 vectors using a TOPO TA Cloning kit (Invitrogen, U.S.A.) to construct pCR2.1-TOPO-GPD2 and pCR2.1-TOPO-RHR2, respectively.

EXAMPLE 3

Cloning of GPD2 Genes into Expression Vectors

1. Amplification of GPD2 Genes

GPD2 genes were amplified by PCR using the pCR2.1-TOPO-GPD2 constructed in Example 2 as a template and a pair of oligonucleotides having nucleotide sequences of SEQ ID NOS: 9 and 10 as primers. The primers having the nucleotide sequences of SEQ ID NOS: 9 and 10 contained restriction sites of NheI and XhoI.

PCR was performed by using 20 μl of a PCR solution prepared by mixing an Accur Power PCR Premix (Bioneer, Korea) with 10 ng of the template and each 100 pmole of the primers (SEQ ID NOS: 9 and 10). PCR conditions were as follows: denaturation at 94° C. for 30 seconds, hybridization at 53° C. for 30 seconds, and polymerization at 72° C. for 1 minute and 30 seconds for 30 cycles.

Amplified PCR products were analyzed by agarose gel electrophoresis. As a result, it was found that 1,129 bp DNA fragments were amplified. After being separated and purified, the DNA fragments were cloned into pCR2.1 vectors using a TOPO TA Cloning kit (Invitrogen, U.S.A.).

2. Cloning of GPD2 Genes into pSE380 Expression Vectors

The pCR2.1 vectors containing the amplified PCR products of the above Section 1 were digested with NheI and XhoI to generate GPD2 genes followed by separation and purification. At the same time, pSE380 expression vectors (Invitrogen, U.S.A.) were digested with NheI and XhoI and then treated with CIP (calf intestinal phosphatase).

1 μl of T4 DNA ligase and 1 μl of a ligase buffer were added to the previously prepared 100 ng of the GPD2 genes and 10 ng of the pSE380 vector restriction fragments and distilled water was added therto to make the total volume 10 μl and then incubated at 16° C. for 6 hours. After the reaction was terminated, *E. coli*DH5 α cells were transformed with the resultant vector products and then GPD2 gene-containing pSE380 vectors were separated and purified from the transformed *E. coli* DH5 α cells.

EXAMPLE 4

Measurement of Enzymatic Activity of GPD2 Proteins

The transformed *E. coli*DH5 α cells obtained in Example 3 were inoculated in a 3 ml LB medium containing each 3 μl of ampicillin and IPTG and cultured at 37° C. for 16 hours. 200 μl R-buffer (0.1 M Tris-maleate, 1 ml DTT, pH 6.5) and lysozyme (1 mg/ml) were added to the culture and suspended. Then, the suspension was mixed with 25 μl chloroform and left on ice for about 5 minutes to obtain a cell-free extract.

Next, 1 ml of 5× dilution of a protein assay solution (Bio-Rad) was added to a 10× dilution of the cell-free extract and incubated for 5 minutes to measure OD values at 595 nm. The total protein concentration of the cell-free extract was calculated by applying the measured OD values to the BSA (bovine serum albumin) standard curve.

The enzymatic activity of the cell-free extract was measured as the follows: first, 100 μl of the cell-free extract, 1 μl of 0.2 M NADH, and 1 μl of 0.2 M dihydroxyacetone phosphate (DHAP) were added to 100 μl of 200 mM Tris/HCl (pH 7.5) and 5 μl of 1 M DTT and then distilled water was added thereto to make a total volume of 1 ml. The reaction solution was incubated at 30° C. for 4 minutes and OD values were measured at 340 nm.

As a result, with respect to control *E. coli* cells transformed with pSE380 vectors, the initial $OD_{340}$ value was 0.270 and the $OD_{340}$ value after 4 minutes of the incubation was 0.274. On the other hand, with respect to the cell-free extract containing GPD2, the initial $OD_{340}$ value was 0.287 and the $OD_{340}$ value after 4 minutes of the incubation was 0.311. The results showed significant difference in the OD values between the control and the test sample. Therefore, it could be seen that the test sample had enzymatic activity (see Table 1 and FIG. 1).

TABLE 1

| Incubation time (min) | Control | GPD2 |
| --- | --- | --- |
| 0 | 0.270 | 0.287 |
| 4 | 0.274 | 0.311 |

EXAMPLE 5

Cloning of RHR2 Genes into Expression Vectors

1. Amplification of RHR2 Genes

RHR2 genes were amplified by PCR using the pCR2.1-TOPO-RHR2 constructed in Example 2 as a template and a pair of oligonucleotides having nucleotide sequences of SEQ ID NOS: 11 and 12 as primers. The primers having the nucleotide sequences of SEQ ID NOS: 11 and 12 contained restriction sites of NheI and XhoI.

PCR was performed by using 20 μl of a PCR solution prepared by mixing an Accur Power PCR Premix (Bioneer, Korea) with 10 ng of the template and each 100 pmole of the primers (SEQ ID NOS: 11 and 12). PCR conditions were as follows: denaturation at 94° C. for 30 seconds, hybridization at 50° C. for 30 seconds, and polymerization at 72° C. for 1 minute and 30 seconds for 30 cycles.

Amplified PCR products were analyzed by agarose gel electrophoresis. As a result, it was found that 778 bp DNA fragments were amplified. After being separated and purified, the DNA fragments were cloned into pCR2.1 vectors using a TOPO TA Cloning kit (Invitrogen, U.S.A.).

2. Cloning of RHR2 Genes into pSE380 Expression Vectors

The pCR2.1 vectors containing the amplified PCR products of the above Section 1 were digested with NheI and XhoI to generate RHR2 genes, followed by separation and purification. At the same time, pSE380 expression vectors (Invitrogen, U.S.A.) were digested with NheI and XhoI and then treated with CIP.

1 μl of T4 DNA ligase and 1 μl of a ligase buffer were added to the previously prepared 100 ng of the RHR2 genes and 10 ng of the pSE380 vector restrictin fragments and distilled water was added thereto to make the total volume 10 μl and then incubated at 16° C. for 6 hours. After the reaction was terminated, *E. coli*DH α cells were transformed with the resultant vector products and then RHR2 gene-containing pSE380 vectors were separated and purified from the transformed *E. coli* DH5 α cells.

EXAMPLE 6

Measurement of Enzymatic Activity of RHR2 Proteins

The transformed *E. coli*DH5 α cells obtained in Example 5 were inoculated in a 3 ml LB medium containing each 3 μl of ampicillin and IPTG and then cultured at 37° C. for 16 hours. 200 μl R-buffer (0.1 M Tris-maleate, 1 ml DTT, pH 6.5) and lysozyme (1 mg/ml) were added to the culture and suspended. Then, the suspension was mixed with 25 μl chloroform and left on ice for about 5 minutes to obtain a cell-free extract.

Next, 1 ml of 5× dilution of a protein assay solution (Bio-Rad) was added to a 10×dilution of the cell-free extract and incubated for 5 minutes to measure OD values at 595 nm. The total protein concentration of the cell-free extract was calculated by applying the measured OD values to the BSA standard curve.

The enzymatic activity of the cell-free extract was measured as the follows: first, 100 μl of 1 M Tricine/HCl (pH 7.0), 2.5 μl of 2 M $MgCl_2$, and 10 μl of 1 M DL-glycerol-3-phosphate were added to 100 μl of the cell-free extract and then distilled water was added thereto to make a total volume of 1 ml. The reaction solution was incubated at 37° C. for 4 minutes and the concentration of inorganic phosphate was analyzed according to Ames method.

As a result, with respect to control *E. coli* cells transformed with pSE380 vectors, the initial $OD_{820}$ value was 0.420 and the $OD_{820}$ value after 4 minutes of the incubation was 0.412. On the other hand, with respect to the cell-free extract containing RHR2, the initial $OD_{820}$ value was 1.628 and the $OD_{820}$ value after 4 minutes of the incubation was 1.691. The results showed significant difference in the OD values between the control and the test sample. Therefore, it could be seen that the test sample had enzymatic activity (see Table 2 and FIG. 2).

TABLE 2

| Incubation time (min) | Control | RHR2 |
|---|---|---|
| 0 | 1.420 | 1.628 |
| 4 | 1.412 | 1.691 |

EXAMPLE 7

Preparation of Polynucleotides Including GPD2 and RHR2 Genes That are Operably Linked and Vectors and Microorganisms Containing the Polynucleotides In this Example, there were prepared vectors containing a polynucleotide including GPD2 and RHR2 genes, each of which was operably linked to a trc promoter and a terminator, and recombinant microorganisms containing the vectors. FIG. 3 illustrates a construction scheme for the polynucleotide and a vector containing the polynucleotide.

1. Preparation of pSE380 Vector Fragments Containing GPD2

The GPD2 gene-containing pSE380 vectors constructed in Example 3 were digested with NdeI and treated with CIP. pSE380 vector fragments containing GPD2 were separated and purified by agarose gel electrophoresis.

2. Preparation of Polynucleotides Including RBS (Ribosomal Binding Site) and RHR2

PCR was performed by using 20 μl of a PCR solution prepared by mixing an Accur Power HL-PCR Premix (Bioneer, Korea) with the RHR2 gene-containing pSE380 vectors constructed in Example 5 as a template and each 100 pmole of primers (SEQ ID NOS: 13 and 14) containing a NdeI restriction site. PCR conditions were as follows: denaturation at 94° C. for 30 seconds, hybridization at 50° C. for 30 seconds, and polymerization at 72° C. for 1 minute and 30 seconds for 30 cycles.

Amplified PCR products were separated and purified by agarose gel electrophoresis and then cloned into pCR2.1 vectors using a TOPO TA Cloning kit (Invitrogen, U.S.A.).

Next, the pCR2.1 vectors were digested with NdeI restriction enzyme to generate polynucleotides including a trc promoter, RHR2 gene, and a terminator, which were then separated and purified by agarose gel electrophoresis (see FIG. 3).

3. Construction of Vectors Containing Polynucleotides including GPD2 and RHR2 That are Operably Linked and Transformation of *E. coli* Cells 1 μl of T4 DNA ligase and 1 μl of ligase buffer were added to the DNA fragments prepared in the Sections 1 and 2 and distilled water was then added thereto to make a total volume of 10 μl. The reaction solution was incubated at 16° C. for 6 hours. *E.coli*DH5 α cells were transformed with the resultant vector products. Then, the vectors were extracted from the transformed *E.coli*DH5 α cells and treated with restriction enzymes to confirm the occurrence of a recombination event. The vectors obtained from the transformed *E.coli*DH5 α cells contained GPD2 and RHR2 genes, each of which included a trc promoter and a terminator, and were designated as pJCR-017. The transformed *E.coli*DH5 α cells were designated as *E.coli*DH5 α (pCJP-017) and deposited in the Korean Culture Center of Microorganisms (KCCM) on May 9, 2003 (accession number: KCCM-10494).

EXAMPLE 8

Production of Glycerol from *E.coli*DH5 α (pCJP-017)

This Example confirmed that the *E.coli*DH5 α (pCJP-017) of Example 7 can produce glycerol in a glucose medium.

First, the *E.coli*DH5 α (pCJP-017) was inoculated on 3 ml of a LB medium containing 3 μl ampicillin and cultured at 37° C. for 16 hours. 1 ml of the culture was added to 50 ml of a glycerol-producing medium and centrifuged at 37° C. at 200 rpm for 48 hours.

The glycerol-producing medium was a sterilized medium (pH 6.7) of 8 g of $KH_2PO_4$, 2 g of $Na_2HP_4$, 0.75 g of $(NH_4)_2SO_4$, 8 g of $(NH_4)_2HPO_4$, 6.6 g of citric acid 2.05 g of $MgSO_4$, 40 mg of $CaCl_2$, 40 mg of $FeSO_4$, and a trace element stock solution, in 1 L distilled water. The trace element stock solution was a sterilized solution of 2 g of $MnSO_4 \cdot H_2O$, 0.8 g of $CoCl_2 \cdot 6H_2O$, 0.4 g of $ZnSO_4 \cdot 7H_2O$, 0.4 g of $Na_2MoO_4 \cdot 2H_2O$, 0.2 g of $CuCl_2 \cdot 2H_2O$, 0.1 g of $H_3BO_3$, and 10 ml of HCl (37%) in 1 L distilled water. The glycerol-producing medium was supplemented with thiamine, antibiotic, and IPTG, in addition to 20 g/L of glucose.

Glycerol and glucose were analyzed using HPLC module type (Waters 510 pump, Waters 717 Autosampler, Waters 400 RI detector, SP 4290 Integrator).

As a result, while no glycerol production was observed in control *E. coli* cells transformed with pSE380 vectors, 4.328 g/l of glycerol was observed in the test cells.

MODE FOR INVENTION

The present invention provides a polypeptide having glycerol-3-phosphate dehydrogenase activity, a polypeptide having glycerol-3-phosphate phosphatase activity, and genes encoding the polypeptides.

The present invention also provides a polynucleotide including a polynucleotide operably linked to a suitable regulatory sequences and encoding a polypeptide having glycerol-3-phosphate dehydrogenase activity and a polynucleotide operably linked to a suitable regulatory sequences and encoding a polypeptide having glycerol-3-phosphate phosphatase activity and a vector containing the polynucleotide.

The present invention also provides a host cell containing the vector and a method for producing glycerol by culturing the host cell.

According to an aspect of the present invention, there is provided a polypeptide having glycerol-3-phosphate dehydrogenase activity and a 80% or more homology to an amino acid sequence of SEQ ID NO: 1. Preferably, the polypeptide has glycerol-3-phosphate dehydrogenase activity and a 90% or more homology to the amino acid sequence of SEQ ID NO: 1. More preferably, the polypeptide has the amino acid sequence of SEQ ID NO: 1.

According to another aspect of the present invention, there is provided a polynucleotide encoding the amino acid sequence of SEQ ID NO: 1. Preferably, the polynucleotide has a nucleotide sequence of SEQ ID NO: 3.

According to another aspect of the present invention, there is provided a polypeptide having glycerol-3-phosphate phosphatase activity and a 80% or more homology to an amino acid sequence of SEQ ID NO: 2. Preferably, the polypeptide has glycerol-3-phosphate phosphatase activity and a 90% or more homology to the amino acid sequence of SEQ ID NO: 2. More preferably, the polypeptide has the amino acid sequence of SEQ ID NO: 2.

According to another aspect of the present invention, there is provided a polynucleotide encoding the amino acid sequence of SEQ ID NO: 2. Preferably, the polynucleotide has a nucleotide sequence of SEQ ID NO: 4.

According to another aspect of the present invention, there is provided a polynucleotide including a first polynucleotide encoding the amino acid sequence of SEQ ID NO: 1 and a second polynucleotide encoding the amino acid sequence of SEQ ID NO: 2 which are operably linked to a suitable regulatory sequence.

According to another aspect of the present invention, there is provided a vector containing a polynucleotide including a first polynucleotide and a second polynucleotide which are operably linked to a suitable regulatory sequence. Preferably, the vector is pCJP-017.

As used herein, the term 'vector' indicates an extrachromosomal element that may carry a nonessential gene for cell metabolism, generally, a double-stranded circular DNA. The extrachromosomal element may be a self-replicating sequence, a genome insertion sequence, a phage or nucleotide sequence, a linear or circular, single- or double-stranded DNA or RNA. Generally, a vector contains a suitable transcription or translation regulatory sequence, a selection marker, or a competent sequence for self-replicating or chromosome insertion. A suitable vector includes a 5'-region of a gene that regulates transcription initiation and a 3'-region of a DNA fragment that controls transcription termination. The term 'suitable regulatory sequence' indicates a sequence that regulates the transcription and translation of the above polynucleotide. Examples of the regulatory sequence include a ribosomal binding sequence (RBS), a promoter, and a terminator. As used herein, the promoter is not particularly limited provided that it is a sequence that drives initiation of transcription of a gene. For example, the promoter may be CYC1, HIS3, GAL1, GAL10, ADH1, PGK, PHO5, GAPDH, ADC1, TRP1, URA3, LEU2, ENO, TPI (useful for expression in *Saccharomyces*), lac, trp, γ $P_L$, γ $P_R$, T7, tac, or trc (useful for expression in *E. coli*). The terminator region may be derived from various genes of a preferred host cell and may be optionally omitted.

According to another aspect of the present invention, there is provided a host cell containing a polynucleotide including a first polynucleotide encoding the amino acid sequence of SEQ ID NO: 1 and a second polynucleotide encoding the amino acid sequence of SEQ ID NO: 2 which are operably linked to a suitable regulatory sequence. The host cell may be a cell of the genus *Escherichia, Citrobacter, Enterobacter., Clostridium, Klebsiella, Aerobacter, Lactobacillus, Aspergillus, Saccharomyces, Schizosaccharomyces,* or *Zygosaccharomyces.* Preferably, the host cell may be a cell of the genus *Escherichia*, and more preferably a cell of *E. coli*.

According to yet another aspect of the present invention, there is provided a method for producing glycerol, which comprises: culturing, in a suitable medium, a host cell containing a polynucleotide including a first polynucleotide encoding the amino acid sequence of SEQ ID NO: 1 and a second polynucleotide encoding the amino acid sequence of SEQ ID NO: 2 which are operably linked to a suitable regulatory sequence; and recovering glycerol from the culture.

The medium includes a 'carbon substrate' or 'carbon source' that can be metabolized in the host cell. The carbon substrate or the carbon source may be selected from the group consisting of monosaccharides, oligosaccharides, polysaccharides, single-carbon substrates, and a mixture thereof.

INDUSTRIAL APPLICABILITY

A polypeptide and a polynucleotide encoding the polypeptide of the present invention can be efficiently used in a recombinant glycerol biosynthetic pathway.

A polynucleotide including GPD2 and RHR2 that are operably linked to a suitable regulatory sequence, a vector and a host cell containing the polynucleotide of the present invention can be used in a method for efficiently producing glycerol. According to this method, glycerol can be produced in high yield.

The invention claimed is:

1. A vector containing a first polynucleotide as set forth in SEQ ID NO: 3 and a second polynucleotide as set forth in SEQ ID NO: 4 which are operably linked to a suitable regulatory sequence.

2. The vector of claim 1, which is a pCJP-017 having a restriction map as shown in FIG. 3.

3. A host cell transformed with a polynucleotide comprising a first polynucleotide as set forth in SEQ ID NO: 3 and a second polynucleotide encoding an amino acid sequence as set forth in SEQ ID NO: 4 which are operably linked to a suitable regulatory sequence, wherein the host cell is *E. coli*.

4. The transformed host cell of claim 3, which is *E. coli* DH5α (pCJP-017) with Accession No. KCCM-10494.

5. A method for producing glycerol comprising:
culturing the host cell of claim 3 in a suitable medium; and
recovering glycerol from the culture.

6. A method for producing glycerol comprising:
culturing the host cell of claim 4 in a suitable medium; and
recovering glycerol from the culture.

* * * * *